ns005491161A

United States Patent [19]
Janssen et al.

[11] Patent Number: 5,491,161
[45] Date of Patent: Feb. 13, 1996

[54] PYRROLOIMIDAZOLYL AND IMIDAZOPYRIDINYL SUBSTITUTED 1H-BENZIMIDAZOLE DERIVATIVES

[75] Inventors: Marcel A. C. Janssen, Vosselaar; Alfons H. M. Raeymaekers, Beerse; Eddy J. E. Freyne, Rumst, all of Belgium; Michael N. Greco, Lansdale, Pa.

[73] Assignee: Janssen Pharmaceutica N.V., Beerse, Belgium

[21] Appl. No.: 450,966

[22] Filed: May 25, 1995

Related U.S. Application Data

[60] Division of Ser. No. 256,465, Jul. 7, 1994, Pat. No. 5,457,102, which is a continuation-in-part of Ser. No. 826,564, Jan. 27, 1992, abandoned.

[51] Int. Cl.$^6$ .................... A61K 31/535; A61K 31/495; A61K 31/435; A61K 31/415
[52] U.S. Cl. .................... 514/394; 514/233.2; 514/253; 514/300; 514/387; 514/388; 514/395; 544/127; 544/362; 546/121; 548/305.4
[58] Field of Search .................... 514/233.2, 253, 514/300, 387, 388, 394, 395; 544/127, 362; 548/305.4; 546/121

[56] References Cited

U.S. PATENT DOCUMENTS 5,066,656  11/1991  Greco et al. .................... 514/269

Primary Examiner—Johann Richter
Assistant Examiner—Laura L. Stockton
Attorney, Agent, or Firm—Charles J. Metz

[57] ABSTRACT

Pyrroloimidazolyl and imidazopyridinyl substituted 1H-benzimidazole derivatives having the formula (I)

wherein
n is 0 or 1;
$R^1$ is hydrogen, nitro, amino, mono- or di($C_{1-6}$alkyl)amino, halo, $C_{1-6}$alkyl, hydroxy or $C_{1-6}$alkyloxy;
$R^2$ is hydrogen; $C_{1-10}$alkyl; $C_{3-6}$alkenyl; $C_{3-6}$alkynyl; $C_{3-7}$cycloalkyl; phenyl; substituted phenyl; $C_{1-4}$alkyl substituted with phenyl, substituted phenyl, naphthalenyl, thienyl, furanyl, $C_{1-4}$alkylfuranyl, $C_{3-7}$cycloalkyl; and
$R^3$ is hydrogen; $C_{1-8}$alkyl; $C_{3-7}$cycloalkyl; hydroxy; amino; $C_{1-6}$alkyloxy; $C_{1-6}$alkyloxycarbonylamino; phenyl; $C_{1-4}$alkyl substituted with phenyl, piperazinyl, 4-($C_{1-4}$alkyl)piperazinyl or morpholinyl;
each substituted phenyl independently is phenyl substituted with a substituent independently selected from halo, hydroxy, hydroxymethyl, trifluoromethyl, $C_{1-6}$alkyl, $C_{1-6}$alkyloxy, $C_{1-6}$alkyloxycarbonyl, carboxyl, formyl, (hydroxyimino)methyl, cyano, amino, mono- and di($C_{1-6}$alkyl)amino and nitro, having sex hormone synthesis inhibiting properties. Compositions containing said compounds of formula (I). Preparations of said compounds and compositions, and use thereof for treating mammals suffering from sex hormone disorders.

4 Claims, No Drawings

PYRROLOIMIDAZOLYL AND IMIDAZOPYRIDINYL SUBSTITUTED 1H-BENZIMIDAZOLE DERIVATIVES

CROSS-REFERENCE TO RELATED APPLICATIONS

This application is a division of application Ser. No. 08/256,465, filed Jul. 7, 1994, now U.S. Pat. No. 5,457,102, which is a 371 of PCT/EP 93/00129, filed Jan. 20, 1993, which is a CIP of U.S. application Ser. No. 07/826,564, filed Jan. 27, 1992, now abandoned.

BACKGROUND OF THE INVENTION

In U.S. Pat. No. 4,617,307 there are described aryl substituted imidazo[1,5-a]pyridines and the corresponding 7,8-dihydro- and 5,6,7,8-tetrahydro-derivatives thereof for use as inhibitors of the enzyme aromatase.

In EP-A-0,293,978, published Dec. 7, 1988, there are described (1H-azol-1-ylmethyl) substituted benzotriazole derivatives as estrogen hormone biosynthesis inhibitory agents. In EP-A-0,426,225, published May 8, 1991, there are described (6,7-dihydro-5H-pyrrolo-[1,2-c]imidazol-5-yl)- and (5,6,7,8-tetrahydroimidazo[1,5-a]pyridin-5-yl) substituted 1H-benzotriazole derivatives as aromatase inhibitors useful in combatting estrogen dependent disorders.

DESCRIPTION OF THE INVENTION

The present invention is concerned with benzimidazole derivatives having the formula

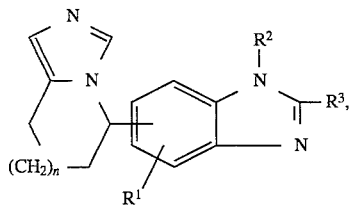

(I)

the pharmaceutically acceptable acid addition salts thereof and the stereochemically isomeric forms thereof, wherein n is 0 or 1;

$R^1$ is hydrogen, nitro, amino, mono- or di($C_{1-6}$alkyl)amino, halo, $C_{1-6}$alkyl, hydroxy or $C_{1-6}$alkyloxy;

$R^2$ is hydrogen; $C_{1-10}$alkyl; $C_{3-6}$alkenyl; $C_{3-6}$alkynyl; $C_{3-7}$cycloalkyl; phenyl; substituted phenyl; $C_{1-4}$alkyl substituted with phenyl, substituted phenyl, naphthalenyl, thienyl, furanyl, $C_{1-4}$alkylfuranyl, $C_{3-7}$cycloalkyl; and $R^3$ is hydrogen; $C_{1-8}$alkyl; $C_{3-7}$cycloalkyl; hydroxy; amino; $C_{1-6}$alkyloxy; $C_{1-6}$alkyloxycarbonylamino; phenyl; $C_{1-4}$alkyl substituted with phenyl, piperazinyl, 4-($C_{1-4}$alkyl)piperazinyl, or morpholinyl;

each substituted phenyl independently is phenyl substituted with a substituent independently selected from halo, hydroxy, hydroxymethyl, trifluoromethyl, $C_{1-6}$alkyl, $C_{1-6}$alkyloxy, $C_{1-6}$alkyloxycarbonyl, carboxyl, formyl, (hydroxyimino)methyl, cyano, amino, mono- and di($C_{1-6}$alkyl)amino and nitro.

As used in the foregoing definitions the term halo is generic to fluoro, chloro, bromo and iodo; the term "$C_{1-4}$alkyl" defines straight and branch chained saturated hydrocarbon radicals having from 1 to 4 carbon atoms such as, for example, methyl, ethyl, 1-methylethyl, 1,1-dimethylethyl, propyl, 2-methylpropyl, butyl and the like; the term "$C_{1-6}$alkyl" defines $C_{1-4}$alkyl radicals as defined hereinabove and the higher homologs thereof having 5 or 6 carbon atoms such as, for example, pentyl, hexyl and the like; "$C_{1-8}$alkyl defines $C_{1-6}$alkyl radicals as defined hereinabove, and the higher homologs thereof having 7 or 8 carbon atoms such as, for example, heptyl, octyl, and the like; "$C_{1-10}$"alkyl defines $C_{1-8}$alkyl radicals as defined hereinabove, and the higher homologs thereof having 9 or 10 carbon atoms such as, for example, nonyl, decyl, and the like; the term "$C_{3-7}$cycloalkyl" defines cyclopropyl, cyclobutyl, cyclopentyl, cyclohexyl and cycloheptyl; "$C_{3-6}$alkenyl" defines straight and branch chained hydrocarbon radicals containing one double bond and having from 3 to 6 carbon atoms such as, for example, 2-propenyl, 2-methyl-2-propenyl, 3-butenyl, 2-butenyl, 2-pentenyl, 3-pentenyl, 3-methyl-2-butenyl and the like; "$C_{3-6}$alkynyl" defines straight and branch chained hydrocarbon radicals containing one triple bond and having from 3 to 6 carbon atoms such as, for example, 2-propynyl, 2-butynyl, 3-butynyl, 2-pentynyl, 4-pentynyl and the like; and when a $C_{3-6}$alkenyl or a $C_{3-6}$alkynyl is substituted on a heteroatom, then the carbon atom of said $C_{3-6}$alkenyl or said $C_{3-6}$alkynyl connected to said heteroatom preferably is saturated.

The 5,6,7,8-tetrahydroimidazo[1,5-a]pyridin-5-yl (n=1) or 6,7-dihydro-5H-pyrrolo[1,2-c]imidazol-5-yl (n=0) moiety of formula

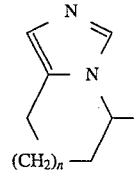

in the compounds of formula (I) as defined hereinabove, may be substituted on any of the 4, 5, 6 or 7 positions of the benzimidazole moiety.

The acid addition salts as mentioned hereinabove are meant to comprise the therapeutically active non-toxic acid addition salt forms which the compounds of formula (I) are able to form. The latter can conveniently be obtained by treating the base form with appropriate acids such as, for example, inorganic acids, such as hydrohalic acid, e.g. hydrochloric, hydrobromic and the like, and sulfuric acid, nitric acid, phosphoric acid and the like; or organic acids such as, for example, acetic, hydroxyacetic, propanoic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be convened by treatment with alkali into the free base form. The term acid addition salt also comprises the hydrates and solvent addition forms which the compounds of formula (I) are able to form. Examples of such forms are e.g. hydrates, alcoholates and the like.

The compounds of formula (I) and some of the intermediates in this invention have an asymmetric carbon atom in their structure. This chiral center may be present in a R- and a S-configuration.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basis molecular structure. Stereochemically isomeric forms of the compounds of formula (I) are obviously intended to be embraced within the scope of this invention.

Interesting compounds are those compounds of formula (I) wherein the 5,6,7,8-tetrahydroimidazo[1,5-a]pyridin-5-yl moiety or the 6,7-dihydro-5H-pyrrolo[1,2-c]imidazol-5-yl moiety is substituted on either the 5 or the 6 position.

A first group of particularly interesting compounds comprises those compounds of formula (I) wherein n=0.

A second group of particularly interesting compounds comprises those compounds of formula (I) wherein n=1.

More particularly interesting compounds within the above groups are those compounds of formula (I) wherein $R^1$ is hydrogen; $R^2$ is hydrogen; $C_{1-10}$alkyl; $C_{3-6}$alkenyl; $C_{3-7}$cycloalkyl; phenyl; $C_{1-4}$alkyl substituted with phenyl or $C_{3-7}$cycloalkyl; and $R^3$ is hydrogen; $C_{1-8}$alkyl; $C_{3-7}$cycloalkyl; hydroxy; amino; $C_{1-6}$alkyloxycarbonylamino; phenyl; $C_{1-4}$alkyl substituted with phenyl; piperazinyl, 4-($C_{1-4}$alkyl)piperazinyl, or morpholinyl.

The most preferred compound is (±)-1-cyclopropyl-6-(6,7-dihydro-5H-pyrrolo[1,2-c]imidazol-5-yl)-1H-benzimidazole, the pharmaceutically acceptable acid addition salts thereof and the stereochemical isomers thereof.

The compounds of formula (I) can generally be prepared from an appropriate aromatic diamine of formula (II) by reaction with an orthoester of formula (III), wherein $R^3$ is as defined hereinabove and $R^4$ represents $C_{1-4}$alkyl, preferably methyl or ethyl.

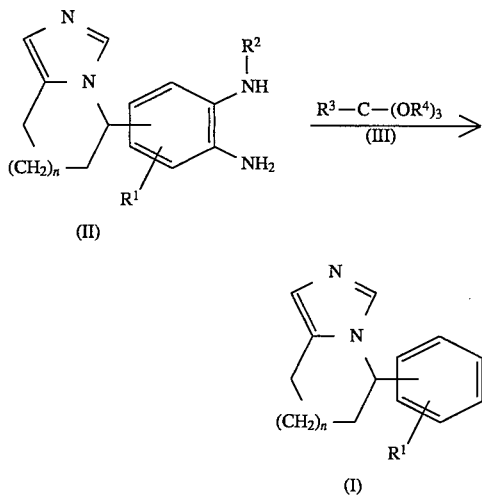

Said reaction can conveniently be conducted by stirring an aromatic diamine of formula (II) in the presence of an orthoester of formula (III), optionally in an excess thereof, in the presence of a mineral or organic acid such as, for example, a hydrohalic acid, e.g. hydrochloric, hydrobromic and the like acids; perchloric acid; perbromic acid; phosphoric acid; sulfuric acid; nitric acid; a carboxylic acid, e.g. formic, acetic, trifluoroacetic, propanoic, benzoic acid and the like; a sulfonic acid, e.g. 4-methylbenzenesulfonic, methanesulfonic and the like acids, optionally in admixture with organic solvents such as, for example, ethers, e.g. 1,1'-oxybisethane, tetrahydrofuran, 1,4-dioxane and the like; alkanols, e.g. methanol, ethanol, propanol and the like; halogenated hydrocarbons e.g. dichloromethane, trichloromethane, 1,1,1-trichloroethane and the like or aromatic hydrocarbons, e.g. benzene, methylbenzene, dimethylbenzene and the like. Somewhat elevated temperatures may enhance the rate of the reaction, more in particular the reaction may be conducted at the reflux temperature of the reaction mixture.

The compounds of formula (I) can also be prepared by reacting an aromatic diamine of formula (II) with a reagent of formula (IV) wherein X is O, S or NH, $R^{3-a}$ represents $R^3$ as defined hereinabove or an appropriate leaving group such as, for example, halogen, imidazole, $C_{1-6}$alkyloxy and the like, and $R^5$ represents an appropriate leaving group such as, for example, hydroxy, halogen, imidazole, $C_{1-6}$alkyloxy, $C_{1-6}$alkylcarbonyloxy, or $C_{1-6}$alkylamino.

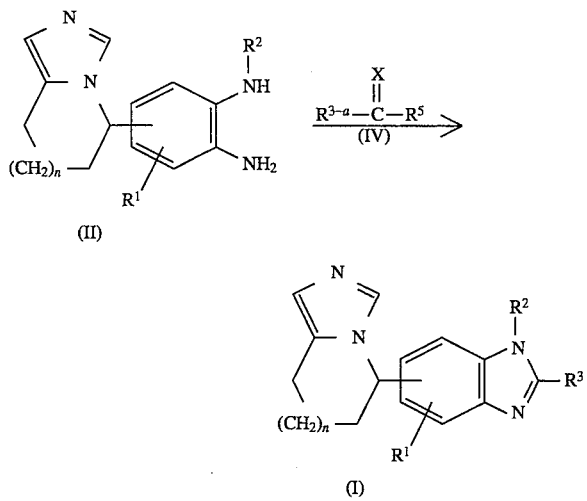

Said reaction can conveniently be conducted by stirring an aromatic diamine of formula (II) in the presence of a reagent of formula (IV), optionally in the presence of an inorganic or organic acid, such as, for example, a hydrohalic acid, e.g. hydrochloric, hydrobromic and the like acids; perchloric acid; perbromic acid; periodic acid; phosphoric acid; sulfuric acid; nitric acid; a carboxylic acid, e.g. formic, acetic, trifluoroacetic, propanoic, benzoic acid and the like; a sulfonic acid; e.g. 4-methylbenzenesulfonic, methanesulfonic and the like acids. An excess of the reagent of formula (IV) or an excess of said acids can be applied as solvent, optionally in admixture with organic solvents such as, for example, alkanols, e.g. methanol, ethanol and the like, halogenated hydrocarbons, e.g. dichloromethane, trichloromethane, 1,1,1-trichloroethane and the like, ethers, e.g. 1,1'-oxybisethane, tetrahydrofuran, 1,4-dioxane and the like or aromatic hydrocarbons, e.g. benzene, methylbenzene, dimethylbenzene and the like. Somewhat elevated temperatures may enhance the ram of the reaction, more in particular the reaction may be conducted at the reflux temperature of the reaction mixture.

The compounds of formula (I) wherein $R^3$ is $C_{1-4}$alkyl substituted with either piperazinyl, 4-($C_{1-4}$alkyl)piperazinyl, said compounds being represented by formula (I-a), or with morpholinyl, said compounds being represented by formula (I-b), wherein m is 1 to 4, Y is O or $NR^6$ and $R^6$ is hydrogen or $C_{1-4}$alkyl, can generally be prepared from an appropriate aromatic diamine of formula (II) by reaction with a reagent of formula (V), wherein X and $R^5$ are as defined hereinabove and W is a reactive leaving group, such as, for example, halo, e.g. chloro, bromo, a sulfonyloxygroup, e.g. methanesulfonyloxy, 4-methylbenzenesulfonyloxy, benzenesulfonyloxy, 2-naphthalenesulfonyloxy, trifluoromethanesulfonyloxy and the like reactive leaving groups, with formation of an intermediate of formula (VI), and subsequent reaction with piperazine, 4-($C_{1-4}$alkyl)piperazine or morpholine of formula (VII), wherein Y and $R^6$ are as defined hereinabove.

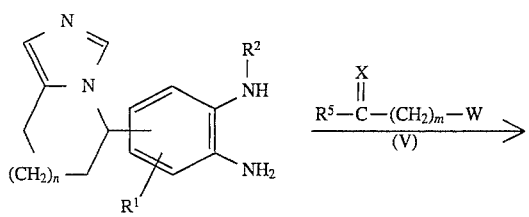

(II)

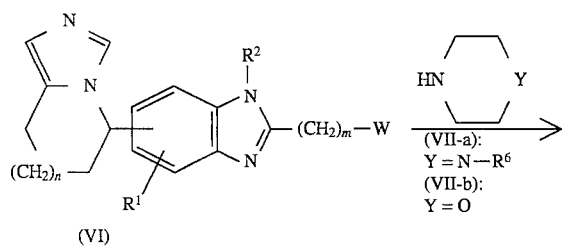

(VI)

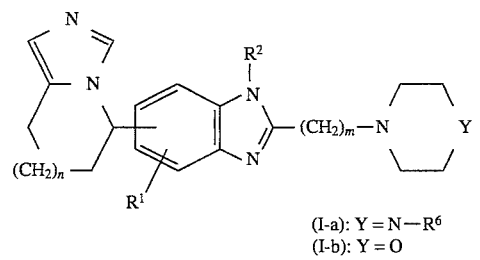

(I-a): Y = N—R⁶
(I-b): Y = O

Said reaction can conveniently be conducted by stirring an aromatic diamine of formula (II) in the presence of a reagent of formula (V), optionally in admixture with an organic solvent, such as, for example, an alkanol, e.g. methanol, ethanol, propanol and the like, at an elevated temperature, preferably at the reflux temperature of the reaction mixture. The thus formed intermediate (VI) is then stirred with a reagent of formula (VII), optionally in admixture with an organic solvent such as, for example, an alkanol, e.g. methanol, ethanol, propanol and the like or an ether, e.g. 1,1'-oxybisethane, tetrahydrofuran, 1,4-dioxane and the like, at an elevated temperature, preferably at the reflux temperature of the reaction mixture.

The compounds of formula (I) may further also be convened into each other following art-known functional group transformations. A number of such procedures will be described in more detail hereinafter.

The compounds of formula (I), wherein $R^2$ is hydrogen, said compounds being represented by formula (I-c), can be prepared by hydrogenolysis of compounds of formula (I), wherein $R^2$ is an optionally substituted benzylgroup, said group being represented by $R^{2-a}$ and said compounds being represented by (I-d), following art-known procedures.

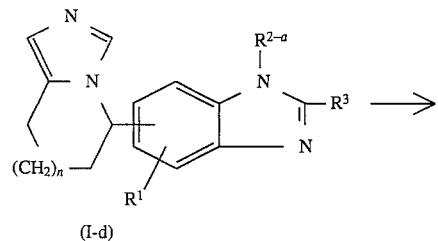

(I-d)

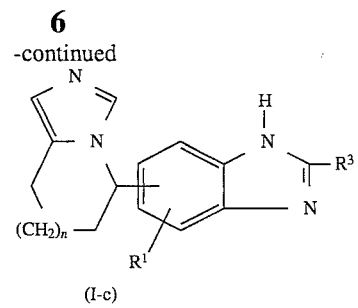

(I-c)

The compounds of formula (I), wherein $R^3$ is amino can be prepared by hydrolysis of compounds of formula (I), wherein $R^3$ is $C_{1-6}$alkyloxycarbonylamino following art-known procedures. The carboxylic acid group of compounds containing said carboxylic group, may be converted into a corresponding ester group following art-known esterification procedures. For example, the carboxylic acid group may be converted into a reactive derivative thereof such as, for example, an acyl halide, an acid anhydride and the like, which is subsequently reacted with a suitable alkanol; or by reacting the carboxylic acid and the alkanol with a suitable reagent capable of forming esters, e.g. dicyclohexylcarbodiimide, 2-chloro-1-methylpyridinium chloride and the like reagents. Conversely, the compounds of formula (I) containing an ester group may be converted into the corresponding carboxylic acids following art-known hydrolysis procedures, e.g. by treating the ester with an aqueous alkaline or aqueous acidic solution.

The compounds of formula (I) wherein $R^3$ is hydroxy may be O-alkylated with a reagent $C_{1-6}$alkyl-W, wherein W is a reactive leaving group as defined hereinabove following art-known O-alkylation procedures.

Compounds of formula (I) containing an alkynyl group may be converted into the corresponding compounds having an alkenyl or alkyl group by catalytically hydrogenating the starting compound in a suitable reaction-inert solvent according to art-known catalytic hydrogenation procedures. Suitable catalysts are for example palladium-on-charcoal, platinum-on-charcoal and the like.

Compounds of formula (I) wherein $R^1$ is hydrogen may be converted into compounds wherein $R^1$ is nitro by stirring the starting compound in a solution of nitric acid in the presence of an appropriate acid, e.g., sulfuric acid, or a mixture of acetic acid and acetic anhydride.

Some of the intermediates and the starting materials in the foregoing are prepared as described in EP-A-0,426,225, published May 8, 1991, and a number of intermediates are novel. A number of such preparation methods will be described hereinafter in more detail.

The intermediates of formula (II) can generally be prepared from the corresponding nitro derivatives of formula (VIII) by reaction with an appropriate reducing agent.

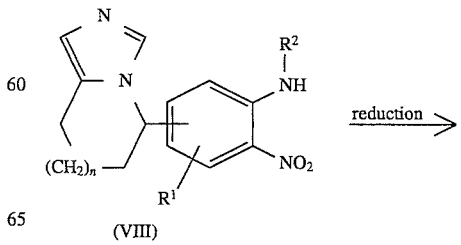

(VIII)

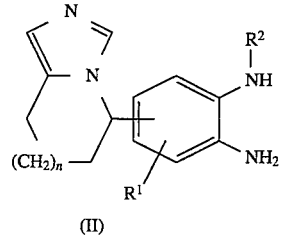

(II)

Suitable reducing agents for the above nitro-to-amine reduction are, for example, hydrazine in the presence of a catalyst like Raney-nickel; or hydrogen in the presence of an appropriate hydrogenation catalyst such as, for example, palladium-on-charcoal, platinum-on-charcoal, Raney-nickel and the like catalysts. Said reduction can conveniently be conducted in a reaction inert solvent such as, for example, an alkanol, e.g. methanol, ethanol, 2-propanol and the like, optionally at an elevated pressure and/or temperature. Alternatively said reduction can also be conducted by reacting the nitro derivative (VIII) with a reducing agent such as sodium dithionite in water optionally in admixture with an alkanol, e.g. methanol, ethanol and the like.

The nitro derivative (VIII) in turn can be prepared from an intermediate (IX) wherein $W^1$ represents a leaving group such as, for example, halo, e.g. chloro, bromo or preferably fluoro, nitro, sulfonyloxy groups, e.g. methanesulfonyloxy, 4-methylbenzenesulfonyloxy and the like, aryloxy, $C_{1-6}$alkyloxy or $C_{1-6}$alkylthio by reaction with a suitable amine of formula (X).

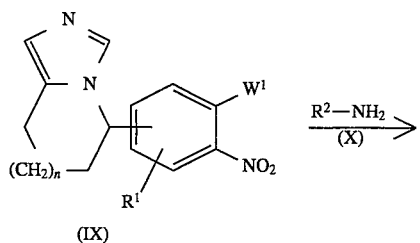

(IX)

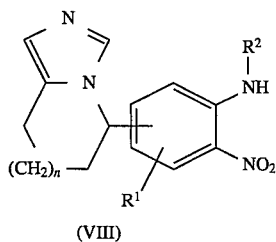

(VIII)

Said reaction can conveniently be conducted by stirring and, if desired, heating the reactants in a reaction-inert solvent such as, for example, an alkanol, e.g. methanol, ethanol, propanol, butanol, 1,2-ethanediol and the like, an ether, e.g. 1,1'-oxybisethane, tetrahydrofuran, 1,4-dioxane and the like, a dipolar aprotic solvent, e.g. N,N-dimethylformamide, dimethylsulfoxide, acetonitrile and the like, a halogenated solvent, e.g. trichloromethane, tetrachloromethane and the like; or a mixture of such solvents. The addition of a suitable base to pick up the acid which is liberated during the reaction may be appropriate; particularly convenient however is the use of an excess of the amine of formula (X).

The intermediates of formula (IX) can conveniently be prepared by nitration of a benzene derivative of formula (XI) following art-known nitration procedures.

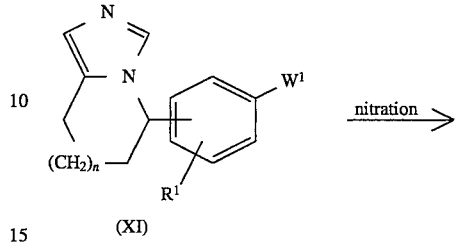

(XI)

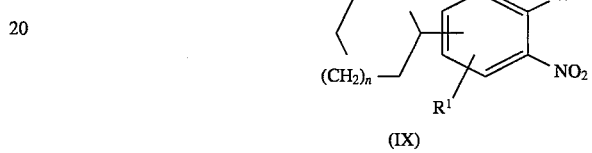

(IX)

For example, said nitration reaction can conveniently be conducted by treating the intermediate (XI) with nitric acid or the nitrate salt of (XI), in the presence of concentrated sulfuric acid at low or ambient temperature. In some instances it may be appropriate to heat the reactants. Said nitration can be conducted without an additional solvent or may also be performed in a suitable solvent such as, for example, a halogenated hydrocarbon, e.g. trichloromethane, tetrachloromethane and the like, a carboxylic acid or a derivative thereof, e.g. acetic acid, acetic anhydride and the like solvents.

The intermediates of formula (XI) can be obtained from an appropriately substituted imidazole of formula (XII) wherein P is a protecting group such as, for example, a trialkylsilyl group, e.g. trimethylsilyl, triethylsilyl, tert. butyldimethylsilyl, and the like, an acyl group, e.g. acetyl, propanoyl and the like, a carbonyl group, e.g. dimethylaminocarbonyl and the like, or a triphenylmethyl group, by first converting the hydroxy group to a leaving group W as defined hereinabove, then cyclizing the thus obtained intermediate (XIII) and simultaneously removing the protecting group P.

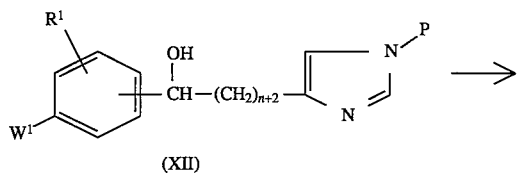

(XII)

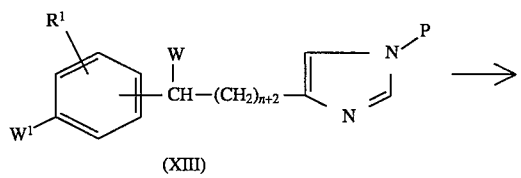

(XIII)

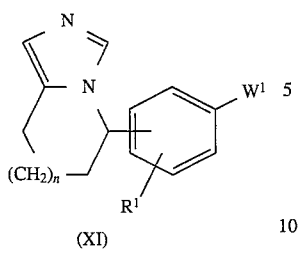

(XI)

Said cyclization and simultaneous deprotection with formation of the intermediates of formula (XI) can be conducted by dissolving and heating the intermediates of formula (XIII) in a reaction-inert solvent such as, for example dipolar aprotic solvents, e.g. acetonitrile, N,N-dimethylformamide and the like, alkanols, e.g. methanol, ethanol and the like, or mixtures of such solvents. Preferably the reaction may be conducted at the reflux temperature of the reaction mixture.

The intermediates of formula (XIII) can easily be obtained from the intermediates of formula (XII) by reaction in a reaction-inert solvent with a halogenating reagent such as, for example, hydrohalic acids, e.g. hydrochloric, hydrobromic and the like acids, phosphorus trichloride, phosphoryl chloride, thionyl chloride and the like, or a sulfonylating reagent such as, for example, methanesulfonylchloride, benzenesulfonylchloride, 4-methylbenzenesulfonylchlofide and the like. Optionally the addition of a suitable base such as, for example, an alkali or earth alkaline metal hydroxide or oxide, e.g. sodium hydroxide, potassium hydroxide and the like, sodium hydride, organic amines, e.g. N-(1-methylethyl)-2-propanamine, N,N-diethylethanamine, 1,8-diazabicyclo[5,4,0]-undec-7-ane and the like bases, may be appropriate to pick up the acid which is liberated during the course of the reaction; particularly convenient is the use of an excess of said organic amines. Suitable reaction-inert solvents are, for example, halogenated hydrocarbons, e.g. dichloromethane, trichloromethane and the like, or ethers, e.g. 1,1'-oxybisethane, tetrahydrofuran, 1,4-dioxane and the like; aromatic hydrocarbons, e.g. benzene, methylbenzene, dimethylbenzene and the like.

The intermediates of formula (XII), wherein $W^1$ is a leaving group such as, for example, $C_{1-6}$alkyloxy, $C_{1-6}$alkylthio, aryloxy, said leaving group being represented by $W^2$, and P is as defined above, said intermediates being represented by formula (XII-a), can be prepared from an appropriately substituted aldehyde of formula (XIV), wherein P is as defined above, by reaction with an organometallic reagent (XV), wherein $W^2$ is as defined hereinabove and M represents a metal group, such as, for example, lithium, halomagnesium, copperlithium and the like.

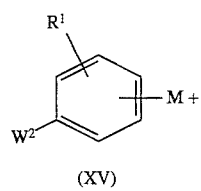

(XV)

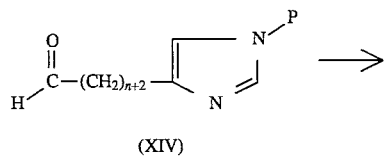

(XIV)

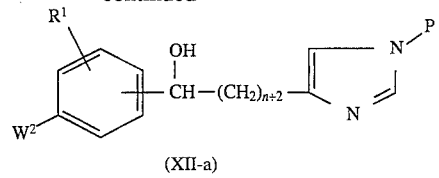

(XII-a)

Said reaction can conveniently be conducted by stirring the organometallic reagent and adding the aldehyde of formula (XIV) in a reaction-inert solvent such as, for example, hydrocarbons, e.g. pentane, hexane and the like; ethers, e.g. 1,1'-oxybisethane, tetrahydrofuran.

The organometallic reagent (XV) may conveniently be prepared by reacting an appropriate phenylhalogenide with a metal such as lithium or magnesium in said solvents.

Pure stereochemically isomeric forms of the compounds of this invention may be obtained by the application of art-known procedures. Diastereoisomers may be separated by physical separation methods such as selective crystallization and chromatographic techniques, e.g. liquid chromatography, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically. Preferably if a specific stereoisomer is desired said compound will be synthesized by stereospecific methods of preparation. These methods will advantageously employ enantiomerically pure starting materials. Stereochemically isomeric forms of the compounds of formula (I) are obviously intended to be included within the scope of the invention.

The compounds of formula (I), the pharmaceutically acceptable acid-addition salts and possible stereochemically isomeric forms thereof inhibit the action of both the enzymes 17-hydroxyl-/17,20-lyase and aromatase. Both said enzymes catalyze subsequent steps in the biosynthesis of estrogens in mammals, i.e. the enzyme 17-hydroxyl-/17,20-lyase catalyzes the formation of androgenic steroids from pregnenolone and progesterone, and the enzyme aromatase catalyzes the conversion of said androgenic steroids into estrogens. Consequently, the subject compounds inhibit the formation of both classes of sex hormones.

The inhibition of estrogen formation from androstenedione and testosterone and the inhibition of androgenic steroids formation from pregnenolone and progesterone can be demonstrated by in-vivo-tests in mammals such as dogs, rats, mice and cats. The in-vivo inhibition of estrogen formation can, for example, be demonstrated by measuring the suppression of the plasma estradiol concentration. The "Estradiol production in PMSG-injected rats"-test, described hereinafter, illustrates the estrogen inhibiting properties of the compounds of formula (I).

The "Testosterone/corticosterone production in LHRH/ACTH-injected rats"-test described hereinafter illustrates the androgenic steroid inhibition properties of the compounds of formula (I). The latter test simultaneously illustrates the fact that corticosterone production in rats is not inhibited by the compounds of formula (I).

In view of theft capability to inhibit the biosynthesis of sex hormones, the subject compounds can be used in the treatment of sex hormone dependent disorders such as, for example, gynecomastia, endometriosis, premature labor, idiopathic oligospermia, endometrial and breast cancers and the like. The beneficial effect of aromatase inhibitors in these disorders are described in, for example, Biochemical Pharmacology, 3 (18), pp. 3113–3219 (1985). Furthermore, the subject compounds, optionally in combination with 5-α-reductase inhibitors, may be particularly useful in treating disorders such as benign prostatic hyperplasia.

The anti-tumour activity of the present compounds of formula (I), especially in estrogen-dependent tumours may be demonstrated in-vivo, for example, by the effect on DMBA-induced Mamma tumours in female Sprague-Dawley rats.

The compounds of the present invention therefore may be used as medicines against sex hormone dependent disorders. The present invention also provides a method of treating mammals suffering from said sex hormone dependent disorders. Said use as a medicine or method comprises the systemic administration to said mammals of an amount, effective to treat sex hormone dependent disorders, of a compound of formula (I), a pharmaceutically acceptable acid-addition salt, or a stereochemically isomeric form thereof. In particular them is provided a method of inhibiting sex hormone synthesis in mammals which comprises the systemic administration to said mammals of a sex hormone synthesis inhibitory amount, more particularly a 17-hydroxyl/17,21-lyase and/or aromatase inhibitory amount, of a compound of formula (I).

The compounds of formula (I), the acid addition salts and the stereoisomeric forms thereof are most preferably administered in the form of appropriate compositions.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprise saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills powder packets, wafers, injectable solutions or suspensions, teaspoonfuls, tablespoonfuls and the like, and segregated multiples thereof.

Those of skill in treating the estrogen dependent disorder could easily determine the effective amount from the test results presented hereinafter. In general it is contemplated that an effective amount would be from 0.0001 mg/kg to 5 mg/kg body weight, and more preferably from 0.001 mg/kg to 0.5 mg/kg body weight.

The following examples are intended to illustrate and not to limit the scope of the invention.

Experimental part

A. Preparation of the intermediates

Example 1 a) To a mixture of 5 g of magnesium in 50 ml of tetrahydrofuran there was added dropwise a solution of 41 g of 1-bromo-4-methoxybenzene in 50 ml of tetrahydrofuran. After stirring for 1 hour at reflux temperature and subsequent cooling to 5° C., there was added a solution of 18.3 g of 1-(triphenylmethyl)-1H-imidazole4-propanaldehyde in 100 ml of tetrahydrofuran. The whole was stirred for 2 hours at room temperature and was then decomposed with an aqueous $NH_4Cl$ solution. The mixture was filtered over diatomaceous earth and the filtrate was extracted with methylbenzene. The organic layer was separated, dried, filtered and evaporated. The oily residue was washed with petroleumether. The petroleumether was decanted and the residue was crystallized from 1,1'-oxybisethane. The product was filtered off and dried, yielding 17.6 g (74.2%) of product. The mother liquor was evaporated and the residue was purified by column chromatography (silica gel; $CH_3COOC_2H_5/CH_3OH$ ($NH_3$) 97.5:2.5). The eluent of the desired fraction was evaporated and the residue was crystallized from 2,2'-oxybispropane, yielding an additional 2.0 g (8.4%) of product. Total yield: 19.6 g (82.6%) of (±)-α-(4-methoxyphenyl)-1-(triphenylmethyl)-1H-imidazole-4-propanol (interm. 1).

b) To a stirred and cooled (0° C.) solution of 19.45 g of intermediate (1) in 100 ml of dichloromethane and 6.28 g of N,N-diethylethanamine there was added a solution of 5.15 g of methanesulfonyl chloride in 50 ml of dichloromethane. After stirring for ½ hour, the reaction mixture was diluted with ice-water. The organic layer was separated, dried, filtered and evaporated. There were added 100 ml of acetonitrile and, after stirring for 3 hours at reflux temperature, 100 ml of methanol. Stirring at reflux temperature was continued for 4 hours. The solvent was evaporated and the residue was dissolved in HCl 1N. The whole was washed with 2,2'-oxybispropane. The aqueous layer was basified with $NH_4OH$ and then extracted with dichloromethane. The extract was dried, filtered and evaporated, yielding 8.5 g (96.8%) of 6,7-dihydro-5-(4-methoxyphenyl)-5H-pyrrolo[1,2-c]imidazole (interm. 2).

c) To a cooled (5° C.) solution of 8.5 g of intermediate (2) in 50 ml of acetic anhydride there were added dropwise 11 ml of nitric acid. The whole was stirred for 1 hour at room temperature and was then poured into a mixture of 500 ml of ice-water and 150 ml of NH₄OH. The product was extracted with dichloromethane and the extract was dried, filtered and evaporated, yielding 10.3 g (99.3%) of (±)-6,7-dihydro-5-(4-methoxy-3-nitrophenyl)- 5H-pyrrolo[1,2-c]imidazole (interm. 3).

d) A solution of 10.3 g of intermediate (3) in 30 ml of 1-butanamine was stirred for 17 hours at reflux temperature. The reaction mixture was evaporated and the residue was taken up in water. The product was extracted with methylbenzene and the extract was dried, filtered and evaporated, yielding 12 g (99.9%) of N-butyl4-(6,7-dihydro-5H-pyrrolo[1,2-c]imidazol-5-yl)-2-nitrobenzenamine (interm. 4).

e) A mixture of 3 g of intermediate (4) and 150 ml of methanol was hydrogenated at normal pressure and room temperature in the presence of 2 g of platinum-on-charcoal catalyst 5%. After the calculated amount of hydrogen was taken up, the catalyst was filtered off and the filtrate was evaporated, yielding 2 g (74.0%) of (±)-$N^1$-butyl-4-(6,7-dihydro-5 H-pyrrolo[1,2-c]imidazol-5-yl)-1,2-benzenediamine (interm. 5).

Example 2 a) A mixture of 3.15 g of 5-(3-chloro-4-nitrophenyl)-6,7-dihydro-5H-pyrrolo[1,2-c]imidazol (prepared as described in EP-A-0,426,225) and 30 ml of cyclopropanamine was stirred for 30 hours at reflux temperature. The reaction mixture was evaporated and the residue was stirred in water. The product was extracted with dichloromethane and the extract was dried, filtered and evaporated. The residue was co-evaporated with methylbenzene, yielding 3.4 g (99.6%) of (±)-N-cyclopropyl-5-(6,7-dihydro-5H-pyrrolo[1,2-c]imidazol-5-yl)-2-nitrobenzenamine (interm. 6).

b) A mixture of 3.4 g of intermediate (6), 2 ml of a solution of thiophene in methanol 4% and 150 ml of methanol was hydrogenated at normal pressure and 20° C. in the presence of 2 g of platinum-on-charcoal catalyst 5%. After the calculated amount of hydrogen was taken up, the catalyst was filtered off and the filtrate was evaporated, yielding 3 g (98.3%) of (±)-$N^2$-cyclopropyl-4-(6,7-dihydro-5H-pyrrolo[1,2-c]imidazol-5-yl)- 2-benzenediamine (interm. 7).

The intermediates listed in Table 1 hereinbelow were prepared in a similar way.

TABLE 1

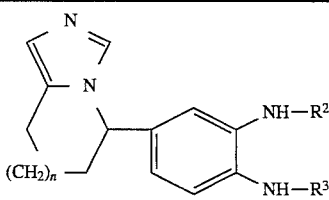

| Interm. No. | n | R² | R³ |
| --- | --- | --- | --- |
| 8 | 0 | —CH₃ | —H |

TABLE 1-continued

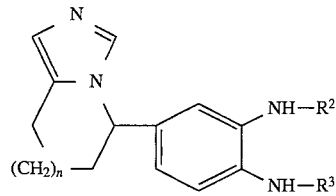

| Interm. No. | n | R² | R³ |
| --- | --- | --- | --- |
| 9 | 0 | —C₅H₁₁ | —H |
| 10 | 0 | —C₆H₁₃ | —H |
| 11 | 0 | —C₃H₇ | —H |
| 12 | 0 | -c.C₆H₁₁ | —H |
| 13 | 0 | —C₆H₅ | —H |
| 14 | 0 | —CH₂—C₆H₅ | —H |
| 15 | 0 | —C₂H₅ | —H |
| 16 | 0 | —CH(CH₃)₂ | —H |
| 17 | 0 | —CH₂—CH=CH₂ | —H |
| 18 | 0 | —H | —H |
| 19 | 1 | —H | —CH₂—C₆H₅ |
| 20 | 0 | —H | —CH₂—C₆H₅ |

B. Preparation of the final compounds

Example 3

A mixture of 3 g of intermediate (7), 25 ml of triethoxymethane and 2.5 ml of formic acid was stirred for 18 hours at room temperature. The reaction mixture was evaporated and the residue was stirred in water. After neutralizing with NH₄OH, the product was extracted with dichloromethane. The extract was dried, filtered and evaporated. The residue was purified by column chromatography (silica gel; CH₂Cl₂/CH₃OH/CH₃OH(NH₃) 97:1.5:1.5). The eluent of the desired fraction was evaporated and the residue was converted into the dinitrate salt in 2-propanol. The salt was filtered off, washed with 2,2'-oxybispropane and dried, yielding 2.5 g. (53.4%) of (±)-1-cyclopropyl- 6-(6,7-dihydro-5H-pyrrolo[1,2-c]imidazole dinitrate; mp. 180.3° C. (comp. 41).

Example 4

A mixture of 3.5 g of $N^2$-butyl-4-(6,7-dihydro-5H-pyrrolo [1,2-c]imidazol-5-yl)- 1,2-benzenediamine (prepared as described in EP-A-0,426,225), 3.9 ml of butanoic acid and 100 ml of HCl 6N was stirred for 10 hours at reflux temperature. The reaction mixture was concentrated, diluted with ice-water and neutralized with NH₄OH. The aqueous layer was separated and extracted with dichloromethane. The extract was dried, filtered and evaporated. The residue was purified by column chromatography (silica gel; CH₂Cl₂/CH₃OH/CH₃OH(NH₃) 97:1.5:1.5). The eluent of 2 product fractions was evaporated and the residues were separately converted into the dinitrate salt in 2-propanol. The salt was filtered off, washed with a mixture of 2-propanol and 2,2'-oxybispropane, and dried, yielding resp. 0.8 g (13.7%) and 1.0 g (17.2%) of (±)-1-butyl-6-(6,7-dihydro-5H-pyrrolo[1,2-c]imidazol-5-yl)-2-propyl-1H-benzimidazole dinitrate; resp. mp. 143.5° C. and 157.0° C. (comp. 45).

Example 5

A mixture of 2.8 g of intermediate (18), 1.6 g of ethyl ethaneimidate and 50 ml of acetic acid was stirred for 18 hours at room temperature. The reaction mixture was evaporated and the residue was taken up in water and neutralized with NH$_4$OH. The product was extracted with a mixture of dichloromethane and methanol (90:10) and the extract was dried, filtered and evaporated. The residue was purified by column chromatography (silica gel; CH$_2$Cl$_2$/CH$_3$OH/ CH$_3$OH(NH$_3$) 95:2.5:2.5). The eluent of the desired fraction was evaporated and the residue was triturated in 1,1'-oxybisethane. The product was filtered off and dried, yielding 0.5 g (16.1%) of (±)-5-(6,7-dihydro-5H-pyrrolo[1,2-c] imidazol-5-yl)-2-methyl-1H-benzimidazole; mp. 229.7° C. (comp. 47).

Example 6

A solution of 3 g of intermediate (19), 2.9 g of ethyl 2-chloroethaneimidate monohydrochloride and 40 ml of ethanol was refluxed for 2 hours. The reaction mixture was evaporated and the residue was stirred in 50 ml of 1,1'-oxybisethane and then dissolved in 40 ml of ethanol. There were added 3.1 ml of 1-methylpiperazine and the whole was refluxed for 3 hours. After cooling, the mixture was diluted with 150 ml of water. The product was extracted with dichloromethane (4×45 ml) and the combined extracts were washed with water, dried, filtered and evaporated. The residue was purified by flash column chromatography (silica gel; CH$_3$COOC$_2$H$_5$/CH$_3$OH/NH$_4$OH 75:20:5). The eluent of the desired fraction was evaporated, yielding 3.0 g (72.4%) of (±)-2-[(4-methyl-1-piperazinyl)methyl]-1-(phenylmethyl)-5-(5,6,7,8-tetrahydroimidazo[1,5-a]pyridin-5-yl)-1H-benzimidazole (comp. 15).

Example 7

A mixture of 4.5 g of N$^2$-butyl-4-(6,7-dihydro-5H-pyrrolo[1,2-c]imidazol-5-yl)- 1,2-benzenediamine (prepared as described in EP-A-0,426,225), 2.5 g of 1,1'-carbonylbis(1H-imidazole) and 100 ml of dry tetrahydrofuran was stirred for 4 hours at room temperature and for 1 hour at reflux temperature. The reaction mixture was evaporated and the residue was stirred in water. The product was extracted with dichloromethane and the extract was dried, filtered and evaporated. The residue was purified by column chromatography (silica gel; CH$_2$Cl$_2$/CH$_3$OH/CH$_3$OH(NH$_3$) 97:1.5:1.5). The eluent of the 2 product fractions was evaporated and the residues were separately triturated in 2,2'-oxybis-propane. The product was filtered off and dried, yielding resp. 0.8 g (19.3%) and 0.9 g (21.7%) of (±)-1-butyl-6-(6,7-dihydro-5H-pyrrolo[1,2-c]imidazol-5-yl)-1H-benzimidazol-2-ol; resp. mp. 170.8° C. and 169.3° C. (comp. 48).

Example 8

To a solution of 1.6 g of compound (14) in some methanol there was added 1,1'-oxybisethane saturated with HCl. The solvent was evaporated and the residue was triturated in 1,1'-oxybisethane and then dissolved in 50 ml of ethanol. This solution was added to a mixture of 3.2 g of palladium(II)hydroxide 20% and 10 ml of ethanol. The whole was hydrogenated for 50 min. at 4.13.10$^5$ Pa and 55° C. After cooling, the catalyst was filtered off and the filtrate was evaporated. The residue was basified with 10% Na$_2$CO$_3$ (aq.). The product was extracted with dichloromethane (4×40 ml) and the combined extracts were washed with water, dried, filtered and evaporated. The residue was purified by flash column chromatography (silica gel; CH$_3$COOC$_2$H$_5$/CH$_3$OH/NH$_4$OH 90:5:5). The eluent of the desired fractions was evaporated and the residue was dissolved in 40 ml of 2-propanol and converted into the nitrate salt by addition of a mixture of 1,1'-oxybisethane and nitric acid. The salt was recrystallized from a mixture of ethyl acetate and 2-propanol, yielding 0.95 g (53.8%) of (±)-2-(2-methylpropyl)-5-(5,6,7,8-tetrahydroimidazo[1,5-a]-pyridin-5-yl)-1H-benzimidazole dinitrate; mp. 176.3° C. (comp. 19).

Example 9

A mixture of 2 of compound (44), 10 ml of NaOH 50% and 100 ml of water was stirred for 1 hour at 80° C. and for 20 hours at 100° C. After cooling on ice, the reaction mixture was successively acidified with acetic acid and treated with NH$_4$OH. The precipitate was filtered off and dissolved in dichloromethane. This solution was washed with water, dried, filtered and evaporated. The residue was purified by column chromatography (silica gel; CH$_2$Cl$_2$/CH$_3$OH/ CH$_3$OH(NH$_3$) 95:2.5:2.5). The eluent of the desired fraction was evaporated and the residue was triturated in 1,1'-oxybisethane. The product was filtered off, washed with 1,1'-oxybisethane and dried, yielding 1.1 g (65.3%) of (±)-1-butyl-6-(6,7-dihydro-5H-pyrrolo[1,2-c]imidazol-5-yl)- 1H-benzimidazol- 2-amine; mp. 195.7° C. (comp. 50).

The compounds listed in Table 2 hereinbelow were prepared following the procedure of the example referred to in the column Ex. No.

TABLE 2

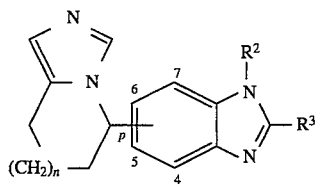

| Comp. No. | Ex. No. | n | p | R$^2$ | R$^3$ | Physical data |
|---|---|---|---|---|---|---|
| 1 | 4 | 1 | 5 | H | H | mp. 267.5° C. |
| 2 | 5 | 1 | 5 | —CH$_2$—C$_6$H$_5$ | C$_2$H$_5$ | MH$^{+(a)}$ = 357 |
| 3 | 8 | 1 | 5 | H | C$_2$H$_5$ | mp. 109.8° C./½ H$_2$O |
| 4 | 5 | 1 | 5 | —CH$_2$—C$_6$H$_5$ | C$_6$H$_5$ | MH$^{+(a)}$ = 405 |
| 5 | 8 | 1 | 5 | H | C$_6$H$_5$ | mp. 241.2° C./HNO$_3$ |
| 6 | 5 | 1 | 5 | —CH$_2$—C$_6$H$_5$ | C$_4$H$_9$ | MH$^{+(a)}$ = 385 |
| 7 | 8 | 1 | 5 | H | C$_4$H$_9$ | mp. 175.0° C./2 HNO$_3$ |
| 8 | 5 | 1 | 5 | —CH$_2$—C$_6$H$_5$ | C$_5$H$_{11}$ | MH$^{+(a)}$ = 399 |
| 9 | 8 | 1 | 5 | H | C$_5$H$_{11}$ | mp. 105.2° C./2 HNO$_3$ |
| 10 | 5 | 1 | 5 | —CH$_2$—C$_6$H$_5$ | C$_3$H$_7$ | mp. 163.9° C./2 HNO$_3$ |

TABLE 2-continued

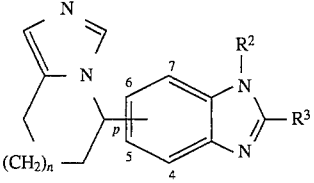

| Comp. No. | Ex. No. | n | p | R² | R³ | Physical data |
|---|---|---|---|---|---|---|
| 11 | 8 | 1 | 5 | H | C₃H₇ | mp. 176.1° C./2 HNO₃ |
| 12 | 5 | 1 | 5 | —CH₂—C₆H₅ | —CH(CH₃)₂ | MH⁺⁽ᵃ⁾ = 371 |
| 13 | 8 | 1 | 5 | H | —CH(CH₃)₂ | mp. 96.9° C./2 HNO₃ ½ H₂O |
| 14 | 5 | 1 | 5 | —CH₂—C₆H₅ | —CH₂—CH(CH₃)₂ | mp. 125.4° C./2 HNO₃ ½ H₂O |
| 15 | 6 | 1 | 5 | —CH₂—C₆H₅ | —CH₂—N(piperazine)N—CH₃ | MH⁺⁽ᵃ⁾ = 441 |
| 16 | 8 | 1 | 5 | H | —CH₂—N(piperazine)N—CH₃ | mp. 151.7° C./H₂O |
| 17 | 6 | 1 | 5 | —CH₂—C₆H₅ | —CH₂—N(morpholine)O | MH⁺⁽ᵃ⁾ = 428 |
| 18 | 8 | 1 | 5 | H | —CH₂—N(morpholine)O | mp. 127.6° C./H₂O |
| 19 | 8 | 1 | 5 | H | —CH₂—CH(CH₃)₂ | mp. 176.3° C./2 HNO₃ |
| 20 | 5 | 1 | 6 | CH₃ | CH₃ | mp. 217.3° C./2 HNO₃ |
| 21 | 3 | 1 | 6 | CH₃ | H | mp. 177.8° C./2 HNO₃ H₂O |
| 22 | 3 | 0 | 6 | C₄H₉ | H | mp. 178.2° C./2 HNO₃ |
| 23 | 3 | 0 | 6 | CH₃ | H | mp. 181.8° C./2 HNO₃ |
| 24 | 5 | 0 | 5 | C₄H₉ | C₆H₅ | mp. 167.8° C./5/2 (COOH)₂ |
| 25 | 3 | 0 | 5 | C₄H₉ | H | mp. 98.6° C./H₂O/2 (COOH)₂ |
| 26 | 5 | 0 | 6 | C₄H₉ | C₆H₅ | mp. 144.6° C. |
| 27 | 5 | 0 | 6 | C₄H₉ | CH₃ | mp. 138.1° C. |
| 28 | 3 | 0 | 5 | —CH₂—C₆H₅ | H | mp. 109.3° C./½ H₂O 2 (COOH)₂ |
| 29 | 5 | 0 | 5 | C₄H₉ | CH₃ | mp. 113.9° C. |
| 30 | 5 | 0 | 5 | —CH₂—C₆H₅ | C₆H₅ | mp. 174.8° C./5/2 (COOH)₂ |
| 31 | 3 | 0 | 6 | C₅H₁₁ | H | mp. 187.3° C./2 HNO₃ |
| 32 | 3 | 0 | 6 | C₆H₁₃ | H | mp. 161.9° C./2 HNO₃ |
| 33 | 3 | 0 | 6 | C₃H₇ | H | mp. 182.7° C./2 HNO₃ |
| 34 | 4 | 0 | 6 | C₄H₉ | C₂H₅ | mp. 158.5° C./2 HNO₃ |
| 35 | 3 | 0 | 6 | c.C₆H₁₁ | H | mp. 202.1° C./2 HNO₃ |
| 36 | 5 | 0 | 5 | —CH₂—C₆H₅ | CH₃ | mp. 168.3° C. |
| 37 | 3 | 0 | 6 | C₆H₅ | H | mp. 184.4° C./2 HNO₃ |
| 38 | 3 | 0 | 6 | —CH₂—C₆H₅ | H | mp. 132.3° C./2 HNO₃ |
| 39 | 3 | 0 | 6 | C₂H₅ | H | mp. 155.5° C./2 HNO₃/½ H₂O |
| 40 | 5 | 0 | 6 | C₄H₉ | c.C₃H₅ | mp. 87.1° C. |
| 41 | 3 | 0 | 6 | c.C₃H₅ | H | mp. 180.3° C./2 HNO₃ |
| 42 | 3 | 0 | 6 | —CH(CH₃)₂ | H | mp. 180.8° C./2 HNO₃ |
| 43 | 5 | 0 | 5 | H | C₆H₅ | mp. 191.2° C./2 HNO₃ ½ H₂O |
| 44 | 5 | 0 | 6 | C₄H₉ | —NH—COOCH₃ | mp. 139.9° C. |
| 45 | 4 | 0 | 6 | C₄H₉ | C₃H₇ | mp. 157.0° C./2 HNO₃ |
| 46 | 3 | 0 | 5 | H | H | mp. 227.4° C. |
| 47 | 5 | 0 | 5 | H | CH₃ | mp. 229.7° C. |
| 48 | 7 | 0 | 6 | C₄H₉ | OH | mp. 170.8° C. |
| 49 | 3 | 0 | 6 | —CH₂—CH=CH₂ | H | mp. 150.7° C./2 HNO₃ |
| 50 | 9 | 0 | 6 | C₄H₉ | NH₂ | mp. 195.7° C. |
| 51 | 5 | 0 | 5 | H | —NH—COOCH₃ | mp. 263.0° C. |

⁽ᵃ⁾: MH⁺ is the m/e-value of the protonated molecular ion, detected by a mass spectrometer, using chemical ionization techniques.

C. Pharmacological examples

Example 10

Estradiol production in PMSG-injected rats

Female Wistar rats weighing 150 g were injected with 200 I.U. Pregnant Mare's Serum Gonadotropin (PMSG) (Folligon®) subcutaneously. Three days later 1 mg/kg of the test compound, dissolved in 20% polyethyleneglycol in water, was administered by garage. Control animals received 20% polyethyleneglycol only. Two hours after drug or placebo administration the animals were killed by decapitation and trunk blood was collected in heparinized tubes. Plasma estradiol was measured using a direct fluorescence immunoassay. The percentage non-recovered estradiol relative to the untreated controls is depicted in the last column of Table 3.

Example 11

Testosterone and corticosterone production in LHRH/ACTH-injected rats

Adult male Wistar rats weighing 250 g were starved 24 h before the start of the experiment. Between 8 and 9 a.m. 10 mg/kg of the test compounds were administered orally by gavage. One hour later, the animals were injected intramuscularly with 40 ng of Luteinizing Hormone Releasing Hormone (LHRH) (Receptal®) and 25 µg of Adrenocorticotropic Hormone (ACTH$_{1-24}$) (Cortrosyn®). To avoid stress, the animals were also anesthetized with 7.5 mg of pentobarbital. Two hours after stimulation, the animals were killed by decapitation and trunk blood was collected in heparinized tubes. Plasma testosterone was determined using direct radioimmunoassay kits with antibody-coated tubes and $^{125}$I-labelled steroids.

Corticosterone was measured using radio immunoassay with $^3$H-labelled corticosterone and dextrane-coated charcoal to separate bound and free steroid.

The percentages of non-recovered testosterone, respectively corticosterone, relative to untreated controls are depicted in the first and second column of Table 3.

TABLE 3

Inhibition of estradiol, testosterone and corticosterone synthesis

| Comp. No. | Testosterone in vivo (% inhibition) 10 mpk/2h | Corticosterone in vivo (% inhibition) 10 mpk/2h | Estradiol in vivo (% inhibition) 1 mpk/2h |
| --- | --- | --- | --- |
| 22 | 92.5 | 35 | 91 |
| 23 | 81 | 31 | 78 |
| 31 | 91 | 28 | 69 |
| 32 | 67 | 37 | 65 |
| 33 | 98 | 55 | 82 |
| 34 | 12 | 21 | 80 |
| 35 | 92 | 22 | 77 |
| 37 | 96 | 22 | 31 |
| 38 | 80 | 7 | 42 |
| 39 | 93 | 39 | 90 |
| 41 | 91 | 39 | 89 |
| 42 | 98 | 33 | 93 |
| 43 | 64 | 20 | 54 |
| 44 | 66 | 10 | 66 |
| 46 | 78 | 23 | 77 |
| 47 | 85 | 4 | 72 |
| 48 | 93 | 4 | 77 |
| 49 | 90 | 13 | 81 |

D. Composition examples

"Active ingredient (A.I.) as used throughout these examples relates to a compound of formula (I), a pharmaceutically acceptable acid addition salt or a stereochemically isomeric form thereof."

Example 12

ORAL DROPS

500 Grams of the A.I. was dissolved in 0.5 l of 2-hydroxypropanoic acid and 1.5 l of the polyethylene glycol at 60°–80° C. After cooling to 30°–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I.. The resulting solution was filled into suitable containers.

Example 13

ORAL SOLUTION

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

Example 14

CAPSULES

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

Example 15

FILM-COATED TABLETS

Preparation of Tablet Core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3- propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

Example 16

INJECTABLE SOLUTION 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I.. The solution was cooled to room temperature and supplemented with water for injection q.s. ad 1 l, giving a solution comprising 4 mg/ml of A.I.. The solution was sterilized by filtration (U.S.P. XVII p. 811) and filled in sterile containers.

Example 17

SUPPOSITORIES

3 Grams A.I. was dissolved in a solution of 3 grams 2,3-dihydroxybutanedioic acid in 25 ml polyethylene glycol 400. 12 Grams surfactant (SPAN®) and triglycerides (Witepsol 555® q.s. ad 300 grams were molten together. The latter mixture was mixed well with the former solution. The thus obtained mixture was poured into moulds at a temperature of 37°–38° C. to form 100 suppositories each containing 30 mg/ml of the A.I.

Example 18

INJECTABLE SOLUTION

60 Grams of A.I. and 12 grams of benzylalcohol were mixed well and sesame oil was added q.s. ad 1 l, giving a solution comprising 60 mg/ml of A.I. The solution was sterilized and filled in sterile containers.

We claim:

1. A method of inhibiting the action of the enzymes 17-hydroxyl-/17,20-lyase and aromatase in mammals, which method comprises administering to said mammals a therapeutically effective amount of a compound of the formula:

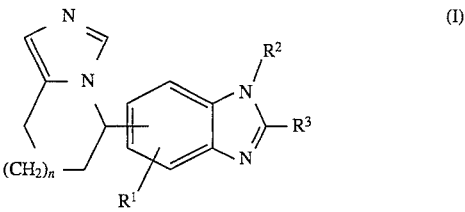

a pharmaceutically acceptable acid addition salt thereof or a stereochemically isomeric form thereof, wherein:

n is 0 or 1;

$R^1$ is hydrogen, nitro, amino, mono-or di($C_{1-6}$alkyl)amino, halo, $C_{1-6}$alkyl, hydroxy, or $C_{1-6}$alkyloxy;

$R^2$ is hydrogen; $C_{1-10}$alkyl; $C_{3-6}$alkenyl, $C_{3-6}$alkynyl, $C_{3-7}$cycloalkyl; phenyl; substituted phenyl; $C_{1-4}$alkyl substituted with phenyl, substituted phenyl, naphthenyl, thienyl, furanyl, $C_{1-4}$alkylfuranyl, or $C_{3-7}$cycloalkyl; and $R^3$ is hydrogen; $C_{1-8}$alkyl; $C_{3-7}$cycloalkyl; hydroxy; amino; $C_{1-6}$alkyloxy; $C_{1-6}$alkyloxycarbonylamino; phenyl; $C_{1-4}$alkyl substituted with phenyl, piperazinyl, 4-($C_{1-4}$alkyl)piperazinyl, or morpholinyl;

wherein each substituted phenyl independently is phenyl substituted with a substituted independently selected from the group consisting of halo, hydroxy, hydroxymethyl, trifluoromethyl, $C_{1-6}$alkyl, $C_{1-6}$alkyloxy, $C_{1-6}$alkyloxycarbonyl, carboxyl, formyl, (hydroxyimino)methyl, cyano, amino, mono- and di($C_{1-6}$alkyl)amino and nitro.

2. A method according to claim 1 wherein the 5,6,7,8-tetra-hydroimidazo[1,5-a]pyridin-5-yl moiety or the 6,7-dihydro-5H-pyrrolo[1,2-c]imidazol-5-yl moiety is substituted on either the 5 or the 6 position of benzimidazole moiety.

3. A method according to claim 2 wherein $R^1$ is hydrogen; $R^2$ is hydrogen; $C_{1-10}$alkyl; $C_{3-6}$alkenyl; $C_{3-7}$cycloalkyl; phenyl; $C_{1-4}$alkyl substituted with phenyl or $C_{3-7}$cycloalkyl; and $R^3$ is hydrogen; $C_{1-8}$alkyl; $C_{3-7}$cycloalkyl; hydroxy; amino; $C_{1-6}$alkyloxycarbonylamino; phenyl; $C_{1-4}$alkyl substituted with phenyl; piperazinyl, 4-($C_{1-4}$alkyl)piperazinyl, or morpholinyl.

4. A method according to claim 1 wherein the compound is 1-cyclopropyl-6-(6,7-dihydro-5H-pyrrolo[1,2-c]imidazol-5-yl)-1H-benzimidazole, a pharmaceutically acceptable acid addition salt thereof or a stereochemically isomeric form thereof.

* * * * *